United States Patent [19]

Faust et al.

[11] Patent Number: 4,853,212
[45] Date of Patent: * Aug. 1, 1989

[54] REDUCED BASE CONTENT CHEWING GUM COMPOSITIONS HAVING ANESTHETIC PROPERTIES

[75] Inventors: Steven M. Faust, Stanhope; Subraman R. Cherukuri, Towaco, both of N.J.

[73] Assignee: Warner-Lambert Company, Morris Plains, N.J.

[*] Notice: The portion of the term of this patent subsequent to Nov. 8, 1988 has been disclaimed.

[21] Appl. No.: 72,303

[22] Filed: Jul. 13, 1987

[51] Int. Cl.$^4$ ............................ A61K 9/68; A23G 3/30
[52] U.S. Cl. ....................................... 424/48; 424/439; 424/440; 426/3; 426/5
[58] Field of Search ..................... 424/48, 439, 440; 426/3, 5

[56] References Cited

U.S. PATENT DOCUMENTS

| | | | |
|---|---|---|---|
| 2,262,087 | 11/1941 | Bartlett et al. | 424/440 |
| 3,011,949 | 12/1961 | Bilotti | 424/48 |
| 4,230,687 | 10/1980 | Sair et al. | 426/534 |
| 4,238,475 | 12/1980 | Witzel et al. | 424/48 |
| 4,610,871 | 9/1986 | Lynch | 424/49 |
| 4,610,872 | 9/1986 | Lynch | 424/49 |

Primary Examiner—Ellis P. Robinson
Assistant Examiner—P. J. Ryan
Attorney, Agent, or Firm—Daniel A. Scola, Jr.; Sandra Gusciora Field

[57] ABSTRACT

This invention relates to reduced base-content chewing gum compositions containing an anesthetic active. These compositions release sufficient amounts of the anesthetic to provide an anesthetic effect in the mount and throat areas without significant bitterness or off-note taste. Hexylresourcinol is the preferred anesthetic.

9 Claims, No Drawings

REDUCED BASE CONTENT CHEWING GUM COMPOSITIONS HAVING ANESTHETIC PROPERTIES

This invention relates to chewing gum compositions capable of providing an anesthetic effect to the mouth and throat areas. More particularly, the compositions of this invention contain an anesthetic-producing active. Due to the high amount of the anesthetic released, these compositions are particularly useful as sore throat remedies.

To produce an effective sore throat chewing gum composition it is necessary that the anesthetic be released in sufficient amounts to provide a numbing effect in the irritated mouth and throat areas. It is a well known phenomenon that a predominate portion of the chewing gum composition, i.e. particularly the flavors and ingredients associated therewith, becomes entrapped in the gum base bolus during mastication. Thus, this concern is also present when actives such as anesthetics are added directly to the gum base. Entrapment of the active in the bolus results in less contact of the active with the mouth and throat areas and a resultant failure to provide effective numbing to the painful areas.

The art has disclosed anesthetics such as hexylresorcinol in lozenge form such that the active is released as the lozenge slowly dissolves in the mouth. The art has not, however, disclosed a chewing gum composition which is designed to provide sufficient release of active to be an effective anesthetic composition, yet be pleasing to taste.

It has been discovered that when the anesthetic is incorporated in a chewing gum composition having a low base-content, there is less tendency of the active to become entrapped in the base since there is less available base. However, the amount of gum base must be at a level which can accommodate other conventional chewing gum ingredients without becoming over-plasticized and producing a gum which falls apart when chewed.

Accordingly the present invention comprises a low base-content chewing gum composition capable of providing an anesthetic effect to the throat and mouth through the release of an anesthetic, said composition comprising, by weight percent:

(a) gum base in the amount of about 16 to about 20%;
(b) flavor to amounts of about 0.5 to about 3%;
(c) sweetener in amounts of about 50 to about 80%; and
(d) anesthetic in an amount sufficient to provide an anesthetic effect to the mouth and throat area.

Generally, this anesthetic is used in a range of up to about 0.5% by weight and preferably in the range of about 0.05 to about 0.5%. More particularly, it is preferred that each gum piece deliver about 1.5 to about 5.0 mg of anesthetic per piece of chewing gum and preferably about 2 to about 2.4 mg.

Those anesthetics useful in the instant invention may be selected from the group generally known as local or topical anesthetics. Preferably the anesthetic is selected from the group consisting of hexylresorcinol, benzocaine, xylocaine, tripelennamine, dibucane, sodium phenolate, tetracaine, chloroprocaine, etidocaine, bupivacaine and mixtures thereof. Pharmaceutically acceptable salts equivalent derivatives of these compounds are contemplated.

The gum base used in this invention may be any water-insoluble gum base well known in the art. Illustrative examples of suitable polymers in gum bases include both natural and synthetic elastomers and rubbers. For example, those polymers which are suitable in gum bases, include, without limitation, substances or vegetable origin such as chicle, jelutong, balata, gutta percha, lechi caspi, sorva, guayale rubber, crown gum and mixtures thereof. Synthetic elastomers such as butadiene-styrene copolymers, isobutylene-isoprene copolymers, polyethylene, polyisobutylene, polyvinylacetate and mixtures thereof, are particularly useful.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene or beta-pinene; terpene resins including polyterpene and mixtures thereof. The solvent may be employed in an amount ranging from about 10% to about 75% and preferably about 45% to about 70% by weight to the gum base.

A variety of traditional ingredients such as plasticizers or softeners such as lanolin, stearic acid, sodium stearate, potassium stearate, glyceryl triacetate, glycerine and the like for example, natural waxes, petroleum waxes, such as polyurethane waxes, paraffin waxes and microcrystalline waxes may also be incorporated into the gum base to obtain a variety of desirable textures and consistency properties. These individual additional materials are generally employed in amounts of up to about 30% by weight and preferably in amounts of from about 3% to about 20% by weight of the final gum base composition.

The chewing gum composition may additionally include the conventional additives of flavoring agents, coloring agents such as titanium dioxide; emulsifiers such as lecithin and glyceryl monostearate; and additional fillers such as aluminum hydroxide, alumina, aluminum silicates, calcium carbonate, and talc and combinations thereof. These fillers may also be used in the gum base in various amounts. Preferably the amount of fillers when used will vary from about 4% to about 30% by weight of the final chewing gum.

The present invention contemplates the inclusion of those sweeteners well known in the art, including both natural and artificial sweeteners. Thus, sweeteners may be chosen from the following non-limiting list: sugars such as sucrose, glucose (corn syrup), dextrose, invert sugar, fructose, and mixtures thereof; saccharine and its various salts such as the sodium or calcium salt; cyclamic acid and its various salts such as the sodium salt; amino acid-based and dipeptide sweeteners such as aspartame; dihydrochalcone compounds; talin; sucralose; glycyrrhizin; *Stevia Rebaudiana* (Stevioside); and sugar alcohols such as sorbitol, sorbitol syrup, mannitol, xylitol, and the like. Also contemplated as an additional sweetener is the nonfermentable sugar substitute (hydrogenated starch hydrolysate) which is described in U.S. Pat. No. Re. 26,959. Also contemplated is the synthetic sweetener 3,6-dihydro-6-methyl-1-1,2,3,-oxathiazin-4-one-2,2-dioxide particularly the potassium (Acesulfame-K), sodium and calcium salts thereof as described in German Pat. No. 2,001,017.7.

In general, the amount of sweetener will vary with the desired amount of sweeteners selected for a particular chewing gum. This amount will normally be 0.001% to about 60% by weight when using an easily extractable sweetener. The water-soluble sweeteners are preferably used in amounts of about 25% to about 60% by weight. In contrast, the artificial sweeteners are used in amounts of about 0.005% to about 5.0% and most preferably about 0.05% to about 2.5% by weight of the final gum composition. These amounts are ordinarily necessary to achieve a desired level of sweetness independent from the flavor level achieved from flavor oils.

Flavoring agents well known to the chewing gum art may be added to the chewing gum compositions of the instant invention. Suitable flavorings include both natural and artificial flavors, and mints such as peppermint, menthol, clove, ginger, oil of Wintergreen, kola flavor, kola extract, artificial vanilla, cinnamon, various fruit flavors and essences, both individual and mixed, and the like are contemplated. The flavorings are generally utilized in amounts that will vary depending upon the individual flavor, and may, for example, range in amounts of about 0.5% to about 3% by weight of the final chewing gum composition weight.

The colorants useful in the present invention include the pigments such as titanium dioxide, that may be incorporated in amounts of up to about 1% by weight, and preferably up to about 6% by weight. Also, the colorants may include other dyes suitable for food, drug and cosmetic applications, and known as F.D. & C. dyes and the like. The materials acceptable for the foregoing spectrum of use are preferably water-soluble. Illustrative examples include indigoid dye, known as F.D. & C. Blue No. 2, which is the disodium salt of 5,5'-indigotindisulfonic acid. Similarly, the dye known as F.D. & C. Green No. 1, comprises a triphenylmethane dye and is the monosodium salts of 4-[4-Nethyl-p-sulfobenzylamino)diphenylmethylene]-[1-(N-ethyl-N-p-sulfoniumbenzyl)-2,5-cyclohexadienimine]. A full recitation of all F.D. & C. and D. & C. and their corresponding chemical structures may be found in the Kirk-Othmer Encyclopedia of Chemical Technology, in Volume 5, at Pages 857–884, which text is accordingly incorporated herein by reference.

The chewing gum formulations are prepared by conventional methods. An illustrative process involves first melting the gum base at a temperature from about 70° C. to about 120° C. and mixing the gum base in a kettle with a liquid softener and/or a emulsifier for 2 to 8 minutes. To this mixture ⅔ to ¾ of the sweetener ingredient and colors are added and mixing is continued for 1 to 4 minutes. To this mixture the remaining sweetener ingredients are added and while mixing is continued, the flavoring agent is slowly added. Mixing is maintained for 1 to 4 minutes. To this mixture a humectant can be added and mixing is continued for 1 to 4 minutes. The gum is discharged from the kettle and formed into its desired shape such as strips, slabs, chunks, ball ropes and/or center filled.

The chewing gum composition of this invention may additionally include the conventional additives of coloring agents such as titanium dioxide; emulsifiers such as lecithin and glyceryl monostearate; and fillers such as dicalcium phosphate, aluminum hydroxide, alumina, aluminum silicates, talc, calcium carbonate, and combinations thereof. The total amount of fillers present is generally up to about 10% by weight. The inventive compositions can be used to prepare sugar or sugarless chewing gums and may be substantially anhydrous as well. Regular and non-adhering (non-stick) formulations are contemplated. Bubble gum, stick gum, pillow shaped, chunk, coated and other gum piece forms well known to the art are contemplated.

The following examples are given to illustrate the invention, but are not deemed to be limiting thereof. All percentages given throughout the specification are based upon weight of the total chewing gum composition unless otherwise indicated.

EXAMPLES

Both inventive compositions (I-1 and I-2) and control compositions (C-1 and C-2) were prepared in accordance with conventional gum-making methods. The inventive compositions had a gum base range of from a minimum 16% to a maximum 20% by weight. Below the minimum range the chewing gum did not have sufficient structural integrity to retain its cohesivity during chew. A sloppy chew resulted with the gum falling apart shortly thereafter. Above the 20% base level, the release properties of the chewing gum composition changed substantially, as evidenced by the significant decline in the percent of anesthetic (hexylresourcinol) released in the control compositions (C-1 and C-2). This is due to a high percentage of the active being entrapped in the bolus of the higher content base.

An expert panel was conducted to determine the relative anesthetic effects of the inventive compositions as compared to the control formulations. Additionally, the percent of hexylresourcinol released during mastication was measured by assaying the gum bolus after the chewout was complete. The results of the expert panel chewouts show a significantly greater percentage of hexylresourcinol being released in the inventive compositions as compared to the controls. This correlates with the marked increased in the anesthetic effect perceived in the throat and mouth of the panelists using the inventive compositions.

|  | % by weight | | | |
| --- | --- | --- | --- | --- |
| Ingredient | I-1 | I-2 | C-1 | C-2 |
| Gum base | 20.00 | 16.00 | 28.00 | 26.00 |
| Emulsifier | 0.50 | 0.50 | 0.50 | 0.50 |
| Sugar | 69.82 | 73.82 | 61.00 | — |
| Sugar alcohol[1] | — | — | — | 55.34 |
| Maltodextrin[2] | 2.50 | 2.50 | 2.50 | — |
| Humectant | 5.00 | 5.00 | 5.00 | 13.5 |
| Flavor | 1.24 | 1.24 | 1.73 | 1.78 |
| Menthol | 0.82 | 0.82 | 1.15 | 1.34 |
| Hexylresourcinol | 0.12 | 0.12 | 0.12 | 0.12 |
| Artificial sweetener (APM) | — | — | — | 1.42 |
| % hexylresourcinol released during 30 minute chewout by expert panel | 79%[3] | — | 48%[3] | 53%[3] |

[1] Mannitol/sorbitol combination
[2] Spherical microporous particles having a bulk density of about 3.0 to about 6.0 lbs./cu. ft.
[3] Represents an average value of chewout by expert panel The invention being thus described, it will be obvious that the same may be varied in many ways. Such variations are not to be regarded as a departure from the spirit and scope of the invention and all such modifications are intended to be included within the scope of the claims.

We claim:

1. A palatable low base-content chewing gum composition capable of providing an anesthetic effect to the throat and mouth through the release of an anesthetic producing active, said composition consisting essentially of in weight percent of the total composition:
   (a) gum base in the amount of about 16% to about 20% wherein the gum base is selected from the group consisting of synthetic gums, natural gums, synthetic elastomers, natural elastomers and mixtures thereof;
   (b) flavor in amount of about 0.5% to about 3%;
   (c) sweetener in the amount of about 50% to about 80%; and
   (d) an anesthetic-producing active present in an amount of from about 0.05% to about 0.5% which is sufficient to provide an anesthetic effect to the mouth and throat areas upon chewing of the composition.

2. The chewing gum composition of claim 1 wherein the anesthetic is selected from the group consisting of hexylresourcinol, benzocaine, xylocaine, tripelennamine, tetracaine, chloroprocaine, etidoaine, bupivacaine, dibucane, sodium phenolate and mixtures thereof.

3. The chewing gum composition of claim 1 wherein the composition is capable of releasing up to about 80% of the anesthetic present.

4. The chewing gum composition of claim 1 wherein the active is in the encapsulated or entrapped form.

5. The chewing gum composition of claim 4 wherein the encapsulating material is microporous maltodextrin having a bulk density of about 3.0 to about 6.0 lbs./cu. ft.

6. The composition of claim 1 wherein the sweetener is selected from the group consisting of water-soluble natural sweeteners, water-soluble artificial sweeteners, dipeptide sweeteners, amino acid-based sweeteners and mixtures thereof.

7. The composition of claim 6 wherein the sweetener is selected from the group consisting of sucrose, fructose, glucose (corn syrup), dextrose, invert sugar; saccharine and its salts; cyclamic acid and its salts; aspartame; dihydrochalcone; glycyrrhizin; *Stevia Rebaudiana* (stevioside); sorbitol, mannitol, xylitol; hydrogenated starch hydrolysate, 3,6-dihydro-6-methyl-1-1,2,3-oxathiazin-4-one-2,2-dioxide (acesulfame-) and its salts; talin; sucralose; and combinations thereof.

8. The composition of claim 1 wherein the flavor is selected from the group consisting of natural flavors, artificial flavors and mixtures thereof.

9. The composition of claim 8 wherein the flavor is selected from the group consisting of peppermint oil, spearmint oil, menthol, clove, ginger, artificial vanilla, cinnamon oil, oil of wintergreen, fruit flavors and essences, kola flavor, kola extract and combinations thereof.

* * * * *

UNITED STATES PATENT AND TRADEMARK OFFICE
CERTIFICATE OF CORRECTION

PATENT NO. : 4,853,212
DATED : August 1, 1989
INVENTOR(S) : Steven M. Faust and Subraman R. Cherukuri It is certified that error appears in the above-identified patent and that said Letters Patent is hereby corrected as shown below:

Title page:

In the abstract, line 4, please correct the spelling of the word "mount" to -- mouth --.

On column 3, line 21, please change "Wintergreen" to -- wintergreen --.

Signed and Sealed this

Ninth Day of July, 1991

Attest:

HARRY F. MANBECK, JR.

*Attesting Officer*  *Commissioner of Patents and Trademarks*